(12) United States Patent
Barki

(10) Patent No.: US 8,715,228 B2
(45) Date of Patent: May 6, 2014

(54) BALLOON CATHETER WITH METAL SHAFT

(75) Inventor: Gerard Barki, Geneva (CH)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 13/357,984

(22) Filed: Jan. 25, 2012

(65) Prior Publication Data

US 2012/0215166 A1   Aug. 23, 2012

(30) Foreign Application Priority Data

Jan. 25, 2011   (EP) .................................. 11 152 014

(51) Int. Cl.
*A61M 29/00*  (2006.01)
*A61M 25/10*  (2013.01)

(52) U.S. Cl.
USPC ........................................ 604/96.01; 604/915

(58) Field of Classification Search
USPC ........................ 604/96.01–103.13, 915–921
See application file for complete search history.

(56) References Cited

U.S. PATENT DOCUMENTS

| | | | |
|---|---|---|---|
| 5,135,516 A * | 8/1992 | Sahatjian et al. ............. | 604/265 |
| 6,033,379 A * | 3/2000 | Barra et al. ............. | 604/103.11 |
| 7,632,242 B2 * | 12/2009 | Griffin et al. ............. | 604/96.01 |
| 2004/0147903 A1 | 7/2004 | Latini | |
| 2007/0167972 A1 * | 7/2007 | Euteneuer et al. ............ | 606/192 |
| 2008/0287786 A1 | 11/2008 | Lentz | |
| 2009/0163780 A1 | 6/2009 | Tieu | |
| 2009/0247945 A1 * | 10/2009 | Levit et al. .................... | 604/103 |

FOREIGN PATENT DOCUMENTS

| | | |
|---|---|---|
| DE | 202007002734 U1 | 4/2007 |
| DE | 202007003734 U1 | 7/2008 |
| WO | 0069502 A1 | 11/2000 |
| WO | 2005092426 A1 | 10/2005 |
| WO | 2007065420 A1 | 6/2007 |

OTHER PUBLICATIONS

European Search Report; Application No. EP 12 15 2048; Issued: Mar. 22, 2012; Mailing Date: Apr. 2, 2012; 6 pages.

* cited by examiner

*Primary Examiner* — Jason Flick
*Assistant Examiner* — Leah Stohr
(74) *Attorney, Agent, or Firm* — St. Onge Steward Johnston & Reens, LLC

(57) ABSTRACT

A balloon catheter has an elongated flexible shaft made of a metal and at least one inflatable balloon mounted on a distal end area of the flexible shaft. A wall of the shaft providing the mechanical properties for flexibility and pushability is entirely made of metal, the wall has a sheet-like shape, and the wall has an outer diameter up to 0.5 mm and a wall thickness in a range from 0.02 mm to 0.1 mm.

40 Claims, 7 Drawing Sheets

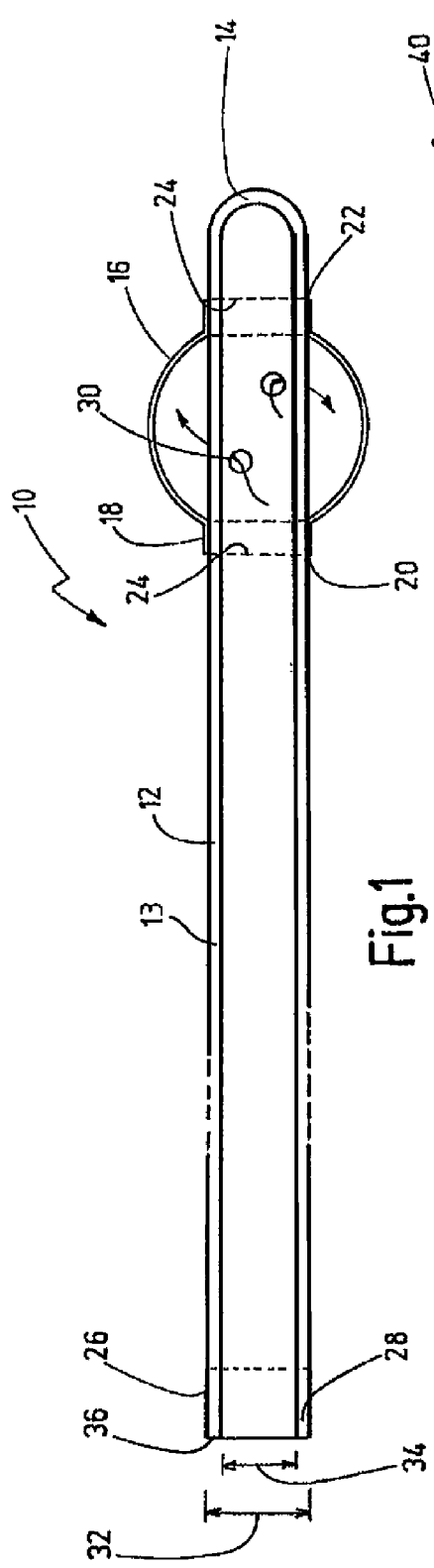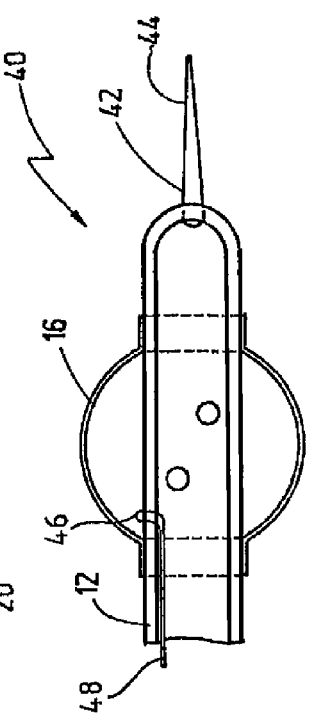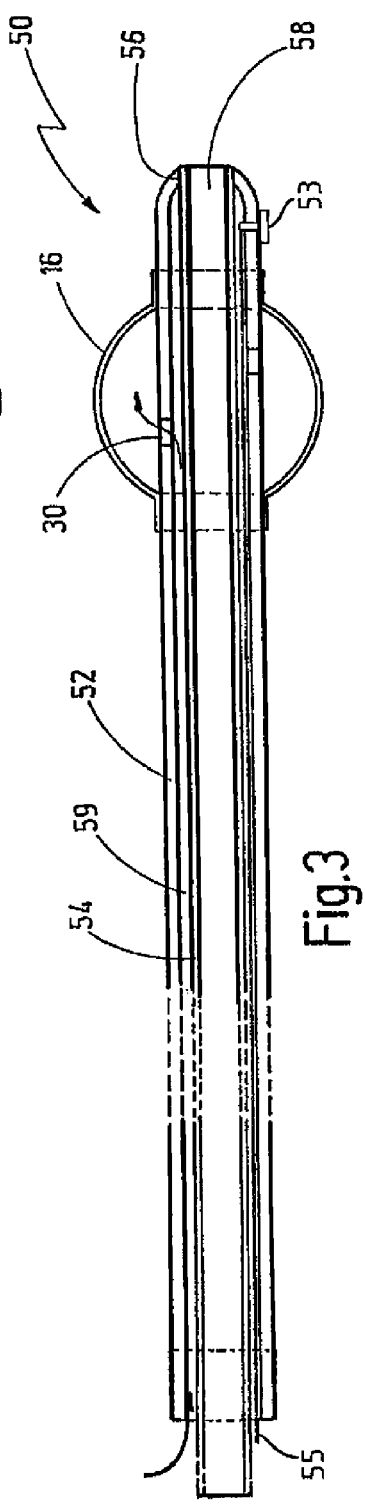

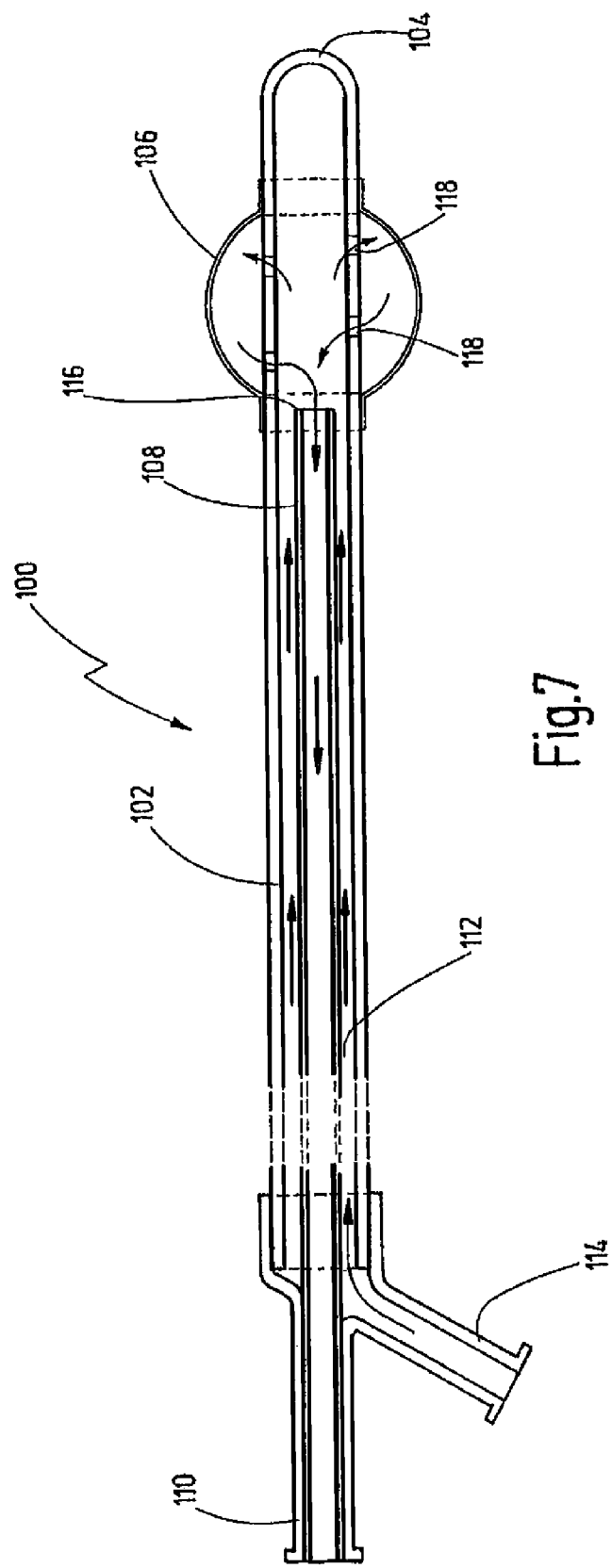

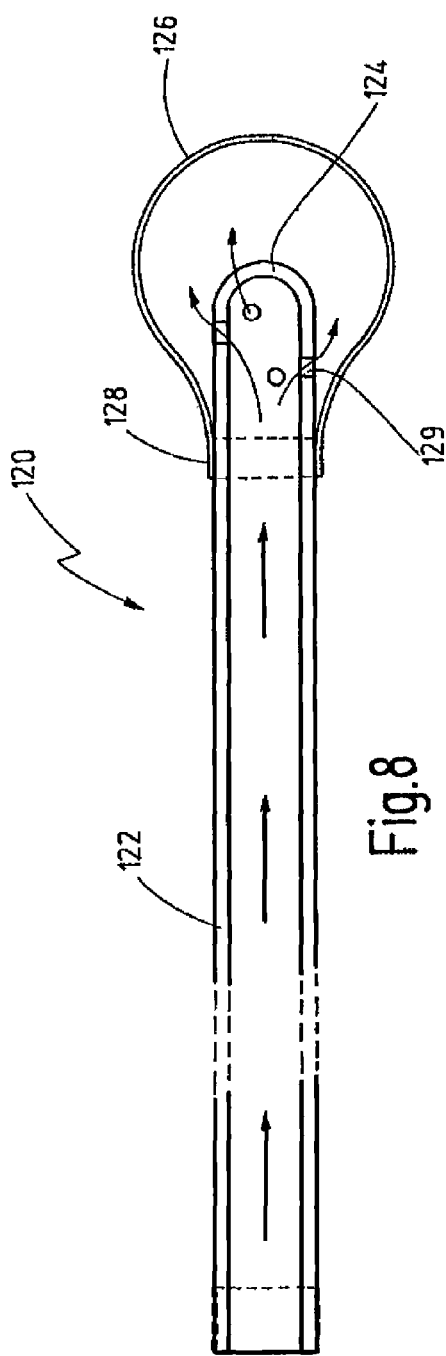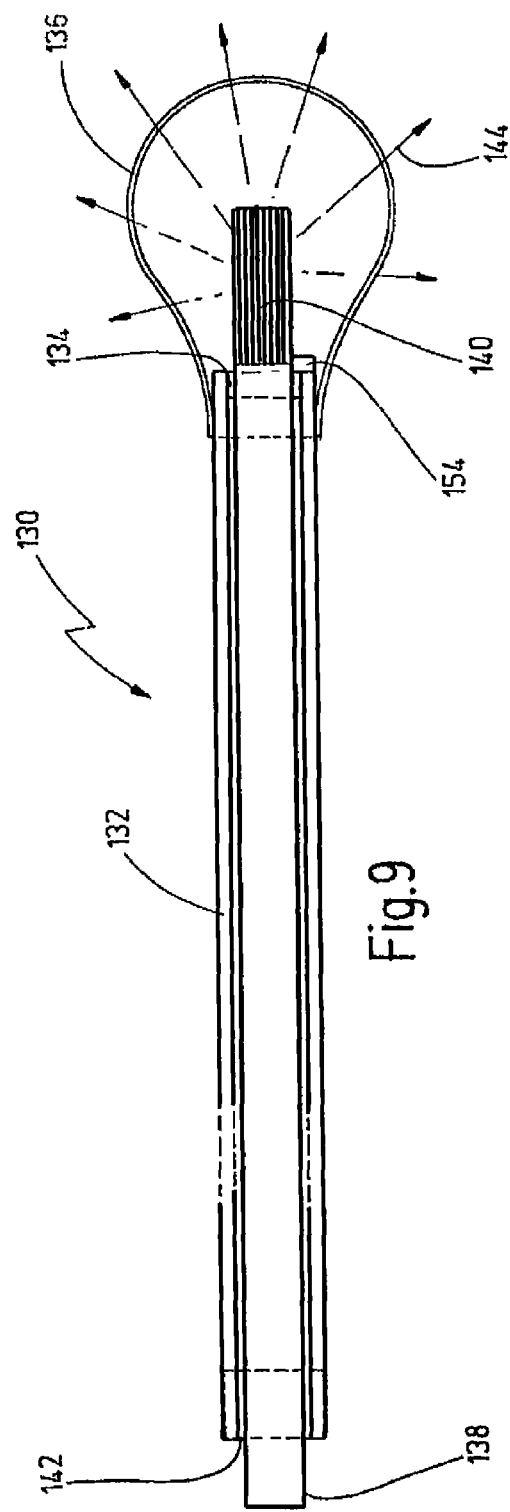

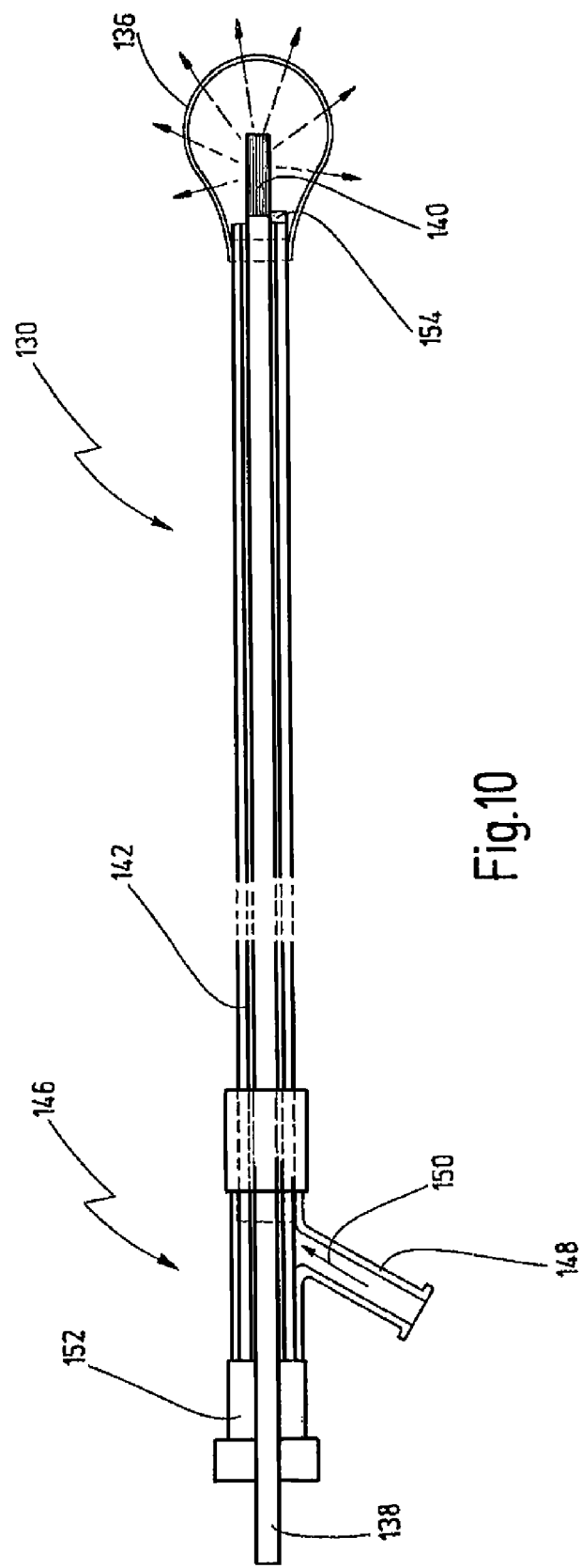

BALLOON CATHETER WITH METAL SHAFT

CROSS-REFERENCE TO RELATED APPLICATIONS

The present application claims priority of European patent application No. 11 152 014.4 filed on Jan. 25, 2011.

FIELD OF THE INVENTION

The present invention relates to a balloon catheter.

BACKGROUND OF THE INVENTION

Balloon catheters are commonly used to treat vascular diseases such as stenotic or narrowed vessels, to place stents for keeping the vessels open or to remove blood clots. Balloon catheters are also used for different purposes such as to dilate stenosis.

Angioplasty techniques typically involve the use of a balloon catheter to dilate constrictions. The balloon catheter is advanced to position the balloon in the stenotic area. The balloon is then inflated and the constriction is dilated. The same technique is used to treat stenosis in salivary ducts. In sialendoscopy this technique is done under vision.

Balloon catheters for use in the medical field can be put in two categories, i.e. low pressure and high pressure.

Low pressure occlusion balloons (usually up to 2 bars) can be used for clot removal. They are known as embolectomy or Fogarty catheters and in some cases they are used for dilation of constrictions in soft tissues. The low-pressure balloons are made of compliant materials, which are soft and expandable materials such as silicon, latex or latex free materials. The balloon is mounted on a polymer shaft, for example from nylon, polyurethane and other polymers. The smallest outer diameters of those catheters are 2 F (1 French=⅓ mm) for the shaft and the diameter of the balloon is in the range of 0.9 mm when not inflated.

High pressure balloon catheters (up to 25 bars) are made of a polymer shaft with or without an inner central working channel. These high pressure balloon catheters are in particular used for coronary angioplasty (PTA, PTCA) and sometimes have a proximal part which is metal tube known also as "hypotube". The tube is fixed to a flexible polymer tube of about 20 cm length. In monorail dilation catheters a small channel is in the flexible polymer tube that allows the passing of a small guide wire. Those high pressure balloon catheters find applications in other fields, for example to dilate stenosis in salivary ducts.

Balloons for high pressure balloon catheters are made out of non compliant materials such as polyester, polyurethane, polyamide or other materials usually considered nonexpendable or at least difficult to expand.

The smallest size of such balloon catheters when not inflated is about 0.80 mm.

WO 2007/065420 A1 discloses catheter tubes for catheters such as angiographic catheters and dilatation catheters. The body of the catheter tube is made of a plastic material which is flexible to allow curved movements of the catheter. The inner surface of the plastic tube is provided with a hard material for minimizing the friction between a guide wire inserted into the catheter tube and its inner side. The inner hard coating materials can be metals, metal alloys, glass, ceramics, metal oxides or mixtures of these materials. The inner layer of hard material may have a tube-like or sheet-like shape with a wall thickness up to 0.0001 mm.

It is the desire in this technology to penetrate with the balloon catheters into very small spaces, ducts, or instrument channels. It was recognized that shafts made of flexible polymers tend to kink if the outer diameter is very small, in particular in the range of 0.5 mm and less.

If such a catheter shaft has kinked once it is very difficult to advance the catheter, particularly if no supporting guide wire is present.

SUMMARY OF THE INVENTION

It is, therefore, an object of the present invention to provide a balloon catheter having a shaft which can be extremely thin, but nevertheless does not bear a high risk of kinking.

This object is achieved by a balloon catheter comprising an elongated flexible metallic shaft and at least one inflatable balloon mounted on a distal end area of said shaft, wherein a wall of said shaft providing the mechanical properties for flexibility and pushability is entirely made of metal, said wall has a sheet-like shape, and wherein said wall has an outer diameter up to 0.5 mm and a wall thickness in a range from 0.02 mm to 0.1 mm.

Due to the smooth metal surface of the wall of sheet-like shape, optimal sealing between the shaft and the balloon is achieved. Shafts having these parameters show flexibility and a very good pushability, without the risk of kinking. Additionally, such a metallic shaft has a high resistance against torsional forces, with the result that it can be pushed in advance within ducts without collapsing due to a twisting. Elongated thin flexible shafts made of metal with the stated parameters do not need a strengthening by additional wires or guide wires which would be needed to avoid the kinking if such small shafts were made of polymers. A shaft with a sheet-like wall entirely made of metal within the given sizes provides the necessary mechanical properties for the use as a balloon catheter. The entire shaft is made of metal, i.e. over its entire length.

A further advantage is that metal tubes are echogenic. This facilitates the surgeon to supervise the path of the catheter within a vessel over its entire length.

In a further refinement of the invention, the outer diameter of the wall of shaft is selected from the group of less than 0.4 mm, less than 0.3 mm or less than 0.2 mm. With such diameters, the shaft can be inserted atraumatically into ducts or vessels.

Such small outer diameters of the shaft enable the introduction of the balloon catheter into small and narrow spaces, ducts, small instrument channels, and into small working channels of flexible, rigid or semi rigid endoscopes.

In a further refinement of the invention, the wall thickness of the shaft is selected from the group of at least 0.025 mm, 0.03 mm, and 0.04 mm.

The increasing wall thickness improves the stability of the hollow shaft body. The stability of the shaft body is always in that the balloon catheter can be used without a core wire.

The greater the outer diameter of the shaft, the more important is the wall thickness to create a hollow tubular body which shows the necessary properties of pushability, resistance against torque and twisting.

In a further refinement of the invention, the metal is stainless steel or a metal alloy, in particular a nickel-titanium alloy. These metallic materials are useful in the medical field and show extreme stability in view of pushability and torque resistance.

In a further refinement of the invention, the distal end of the shaft is closed and small holes are drilled or lasered in the wall in the distal end area of the shaft where the balloon is mounted.

This results in a very stable and simple construction of the balloon catheter. The holes allow the passage of either gas or liquid, to inflate the balloon. Small holes do not remarkably reduce the pushability, in particular in the distal end area. The sizes of the holes may vary from 0.05 mm to 0.2 mm.

The closed distal end reinforces the shaft body at the distal end area and provides an atraumatic tip.

In a further refinement of the invention, a flexible tip projects from the distal end of the shaft.

The flexible tip allows the surgeon to introduce the catheter tip into small channels. The flexible tip can be fixed to the distal end of the shaft.

In a further refinement of the invention, the tip is a flexible guide wire.

A flexible guide wire allows the surgeon to exactly target a path for advancing the catheter. If the flexible guide wire is made of metal, this can be controlled from the outside via ultrasound or the like.

In a further refinement of the invention, the diameter of the tip is smaller than the outer diameter of the shaft.

This measure has the advantage that this allows to first insert the tip into extreme small openings. A further advancement allows to insert the larger tube into extremely small spaces guided by the smaller flexible tip.

In a further refinement of the invention, an inner tube is housed in the shaft, the inner tube being open at its distal end and defining a central working channel passing through the shaft.

This measure has the advantage that the working channel can serve for several manipulations necessary during the surgery. For example, the working channel can allow a passage of a therapeutic drug. The working channel can enable the passage of small wires, laser fibers, light guide fibers, sensors, image guides or microendoscopes. If the microendoscope can transmit light for illumination or for use in Photo Dynamic Diagnosis (PDD) or Photo Dynamic Therapy (PDT), it is possible to both transmit an image from the distal end of the catheter and make diagnostic or treating performances.

In a further refinement of the invention, the outer diameter of the inner tube is smaller than an inner diameter of the shaft, thereby defining a supply channel for supplying an inflating medium to the balloon, the supply channel opens into the balloon.

This measure has the remarkable advantage that the resulting supply channel, which is the space between the outer side of the inner tube and the inner side of the outer shaft, can serve to supply the inflating medium.

In a further refinement of the invention, an inner tube is housed in the shaft, said inner tube is closed at its distal end, and the inner tube and the shaft are provided with openings in an area where the balloon is mounted thereon.

This measure has the remarkable advantage that, with two channels, one can serve for supplying an inflating medium, in particular a liquid, and the second one for escaping or discharging a medium, mostly air, contained within the inner lumen of the catheter system.

If one uses the high pressure technology, a liquid is usually used for inflating the balloon. But, in the system there are amounts of air. With the two channel constructions it is possible to supply or insert the liquid medium via one channel into the catheter and to allow the air to escape via the other channel. For example, it is possible to insert the inflation liquid via the inner tube to inflate the balloon and to simultaneously discharge the air via the outer channel, i.e. the channel between the outer side of the inner tube and the inner side of the shaft.

This can also be done vice versa, i.e. to introduce the inflating liquid medium via the outer tube and to discharge the air via the inner tube.

In a further refinement of the invention, an inner tube is housed in the shaft, the shaft is closed at its distal end and the inner tube is open at its distal end, and the inner tube ending at a distance to the closed end of the shaft.

This measure has the advantage that it is possible to insert a liquid inflating medium via the inner tube to fill the space in the shaft in the area where the balloon is mounted thereon. Air present in the system is able to escape via the outer channel. When inflating the balloon, the liquid can directly penetrate via the openings in the shaft out of the distal end area of the shaft into the balloon and can inflate it.

In a further refinement of the invention, at least one balloon has the shape of a hose section and is mounted on its two opposite ends on an outer surface of the shaft.

This measure allows designing balloons of a desired length.

In a further refinement of the invention, the outer surface of the shaft is roughened in at least that area where the balloon is mounted.

Metal shafts usually show a very smooth surface. The balloon which is made of latex, latex-free polymers or copolymers, nylon, polyester or any plastic material, has to be secured to the outer side of the shaft. A roughening of the shaft in these areas allows a better fixing of the balloon body at the outside of the shaft, for example by gluing or the like. The roughening as such can be made via sand blasting or the like. The balloon as such can have various shapes.

In a further refinement of the invention, the shaft is roughened on its proximal end section.

This roughening allows to connect the proximal end of the metal tube with fittings or the like made of plastic, for example, fittings like Tuohy Borst Y-connectors or haemostasis valve Y connectors.

In a further refinement of the invention, the shaft is open at its distal end, and a balloon having one open end is mounted to the open distal end of the shaft.

This results in a very simple construction of the balloon catheter.

The balloon can be mounted via its neck around the single open end at the outer side of the distal end area of the shaft. The open end of the shaft is the supply discharge opening for introducing the inflating medium into the balloon for inflating it. This can be a gaseous or a liquid inflating medium.

In a further refinement of the invention, a further tube is mounted in the supply channel between shaft and inner tube, the further tube divides the supply channel into two subchannels, each subchannel is in communication with at least one balloon.

This measure has the remarkable advantage that the entire inner hollow space of the inner tube can be used as a working channel. The supply channel, i.e. the space between the outer face of the inner tube and the inner face of the outer shaft, is now subdivided by the further tube into two subchannels. These two subchannels can be used for supplying the inflating medium and for discharging or escaping air present in the inner lumen of the catheter shaft system.

As described above, either the inner or the outer one of the two subchannels can now be used as a supply channel for supplying the inflating medium, in particular a liquid, and the other subchannel can be used for discharging air present in the system.

In a further refinement of the invention, each of the subchannels is connected to a fitting at its proximal end.

This measure has the advantage, that each of the two subchannels can be used either as a supply channel or as a discharge channel, whatever is appropriate. In practical use, the subchannel used for discharging the air can be open to the outside at first, as long as a liquid inflating medium is introduced into the system. After all air is discharged or escaped, this channel can be closed, and a further introduction of the liquid inflating medium now causes inflating of the balloon. For discharging the inflating medium, the channel can be opened.

This reflects a high flexibility and a great application field of the balloon catheter of the present invention.

In a further refinement of the invention, the shaft has a coating at its outer side made of a material of a slow slide resistance, and/or a drug.

This measure has the advantage, that the sliding of the catheter within the vessel is improved by a slow-slide resistance coating.

A drug released by the coating can support the surgery or support the later healing process.

The closed advancing end of the shaft can be rounded to allow a less dramatic advancement of the distal end area of the shaft. The invention requires that the shaft, which is always the outer shaft, is made of metal. In the embodiments having additional inner tubes or additional tubes, one is free to choose the material of these additional tubes. These tubes can also be made of metal or can be made of plastic.

If the outer tube made of metal according to the invention withstands against kinking, torsion or twisting movements, an inner shaft made of plastic also does not undergo the undesired deformations.

In a further refinement of the invention, the shaft is provided with one or more sensors, in particular temperature, pressure, leakage flow or analyzing sensors.

The provision of such sensors has the advantage that temperatures, or flow capacities of the medium supplied through the balloon catheter system, can be supervised and controlled. Losses or the like can be detected via such sensors.

It will be understood that the features of the invention mentioned above and those yet to be explained below can be used not only in the respective combination indicated, but also in other combinations or in isolation, without leaving the scope of the present invention.

BRIEF DESCRIPTION OF THE DRAWINGS

Exemplary embodiments of the invention are explained in more details in the following description and are represented in the drawings, in which:

FIG. 1 shows a longitudinal section of a first embodiment of a balloon catheter, FIG. 2 shows a similar view, but only in the distal end area of a second embodiment with a projecting tip, FIG. 3 shows a longitudinal section of a third embodiment of a balloon catheter with a working channel, FIG. 7 shows a longitudinal section of a sixth embodiment of a balloon catheter with a fitting at its proximal end, FIG. 8 shows a seventh embodiment of a balloon catheter, FIG. 9 shows a similar view of an eighth embodiment of a balloon catheter with an illumination rod, FIG. 10 shows the embodiment of FIG. 9 with a fitting at its proximal end.

DETAILED DESCRIPTION OF THE INVENTION

Figure 4:
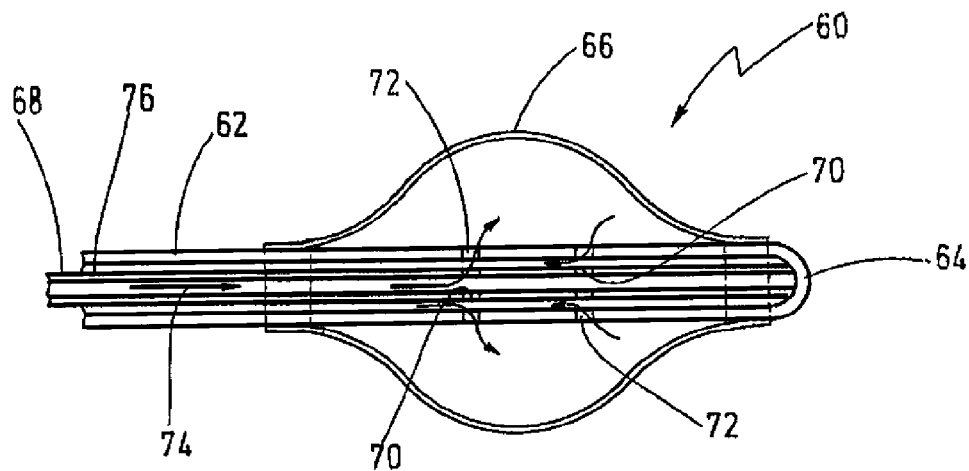
FIG. 4 shows a longitudinal section of a fourth embodiment of a balloon catheter in the distal end area.

FIG. 1 shows a first embodiment of a balloon catheter which is entirely designed with reference numeral 10.

The balloon catheter 10 has an elongated flexible shaft 12 with a length of about 40 cm. A distal end 14 of the shaft 12 is closed and rounded.

A balloon 16 is mounted on the outer face of the flexible shaft 12 in the distal end section of the flexible shaft 12.

The balloon 16 has the shape of a hose section 18. The two opposite ends 20 and 22 are glued to the outer face of the flexible shaft 12.

In this area, the outer surface of the shaft 12 is provided with a roughening 24. A further circumferential roughening 26 is provided at the proximal end 28 of the flexible shaft 12. The roughenings 24 and 26 are made by sand blasting.

Holes 30 are provided in the wall of the flexible shaft 12 in the area where the balloon 16 is mounted. The holes 30 are through bores in the wall of the flexible shaft 12 with a diameter of 0.1 to 0.2 mm.

These holes 30 can be drilled or lasered in the shaft 12, and the size can vary from 0.05 mm up to 0.2 mm. The sand blasting allows a strong gluing of the balloon 16. The balloon 16 can also be hot-melted or fixed via threads or the like at the outer side of the shaft 12.

A wall 13 of the flexible shaft 12 is entirely made of metal, stainless steel, i.e SS304, or a nitinol alloy. The outer diameter 32 of the example shown is 0.40 mm, the inner diameter 34 is 0.25 mm. This results in a wall thickness 36 of 0.075 mm. The wall 13 of the shaft has a sheet-like shape with a smooth surface, by which optimal sealing between the shaft and the balloon is achieved.

In a similar embodiment, the outer diameter is 0.35 mm and the inner diameter is 0.22 mm. An inflating medium, for example a liquid, can be introduced into the flexible shaft 12 from its open proximal end. The inflating medium penetrates the holes 30 and causes inflating of the balloon 16 between its fixed ends 20 and 22, as shown in FIG. 1.

In the second embodiment shown in FIG. 2, the balloon catheter 40 has a flexible shaft 12 that is similar to the shaft described with balloon catheter 10, therefore, the same reference numerals are used. The design of holes and balloon is also similar.

The closed rounded end 14 is provided with a tip 42.

The tip 42 is a piece of the guide wire 44 of metal that is welded with the shaft body. The guide wire 44 has a diameter of about 0.15 mm and can have a length from 5 mm to 10 cm. The length of the guide wire 44 is adapted to the necessity of the procedure. In an interior of the balloon 16 a pressure sensor 46 is mounted. The pressure sensor 46 takes the actual pressure within the balloon 16 during inflating the balloon 16. This actual pressure differs remarkably from the pressure exerted at the proximal end of the respective supply channel. This pressure measurement allows to avoid a burst of the balloon 16 due to an overpressure within the balloon 16. A cable 48 transmits the pressure data to the proximal end of the balloon catheter 10.

In FIG. 3, a third embodiment of a balloon catheter 50 is shown. The flexible shaft 52 is open at its distal end 56, and an inner tube 54 is inserted into the shaft 52. The distal ends 56 of flexible shaft 52 and inner tube 54 are connected together, for example by welding or gluing. A balloon 16 is mounted at the distal end area of flexible shaft 52 as described before. The outer diameter of the flexible shaft 52 is 0.4 mm, the inner diameter is 0.3 mm. The shaft 52 is made entirely of nitinol. The outer shaft 52 as such provides the mechanical properties for flexibility and pushability.

In one embodiment, the inner tube 54 is entirely made of metal and has an outer diameter of 0.25 mm and an inner diameter of 0.17 mm. In this case the distal ends of shaft 12 and tube 54 are welded together.

In another embodiment, the inner tube 54 is made of polyimide and has an outer diameter of 0.25 mm and an inner diameter of 0.20 mm.

The inner tube 54 defines a central working channel 58 passing the entire balloon catheter 60.

Between an outer side of the inner tube 54 and an inner side of the outer flexible shaft 52, a supply channel 59 exists.

It is possible to supply an inflating medium, for example a liquid, from the proximal end of the supply channel 59 up to the holes 30 in the flexible shaft 52. This inflating medium now penetrates into the balloon 16 and inflates the balloon 16.

Independently of the operation stage of the balloon 16, it is always possible to perform manipulations through the central working channel 58.

An analyzer 53 is mounted at an outside of the shaft 52, preferably at the tip or close to the tip of the shaft. The analyzer 53 can analyze blood composition data and/or gas data like oxygen content of liquids in the channels or vessel into which the balloon catheter 50 is inserted. The data are transmitted via a cable 55 which transmits the taken data to the proximal end of the balloon catheter 50. The cable may run along the inside or the outside of the shaft. It is also possible that the cable is executed as a printed circuit track on the surface of the shaft. Alternatively, a wireless type sensor may be used, so that the cable is only necessary for the power supply of the sensor. These data allow to determine high risk factors at the distal end of the inserted balloon catheter 50. If such high risk factors are sensed, the use of the balloon catheter may be interrupted. The analyzer 53 is mounted proximally to the balloon 16 close to the distal end 56 of the shaft 52.

FIG. 4 shows a fourth embodiment of a balloon catheter 60. The balloon catheter 60 has an elongated flexible shaft 62 which is closed at its distal end.

A balloon 66 is mounted at the outer side of the flexible shaft 62, as described before. An inner tube 68 is inserted into the flexible shaft 62 and its distal end ends at the inner side of the closed distal end 64 of the flexible shaft 62. Holes 70 are provided in the wall of the inner tube 68 in an area where the balloon 66 is mounted.

Holes 72 are provided in the wall of the flexible shaft 62, in an area where the balloon 66 is mounted.

It can be seen that holes 70 and 72 are aligned in radial direction.

As shown in FIG. 4, it is possible to introduce an inflating medium 74, for example a liquid, via the inner tube 68. This inflating medium 74 first penetrates the holes 70 in the inner tube 68 and then the holes 72 in the shaft 62. The inflating medium 74 now causes the balloon 66 to inflate.

Air which is present in the system can escape via an escape channel 76 present between the outside of inner tube 68 and the inner side of outer shaft 62. In operation, the air may be urged first into the balloon 66. However, the more liquid as an inflating medium 74 is introduced into the balloon 66, the more air escapes via the escape channel 76 to the proximal end of the escape channel 76.

Figure 5:
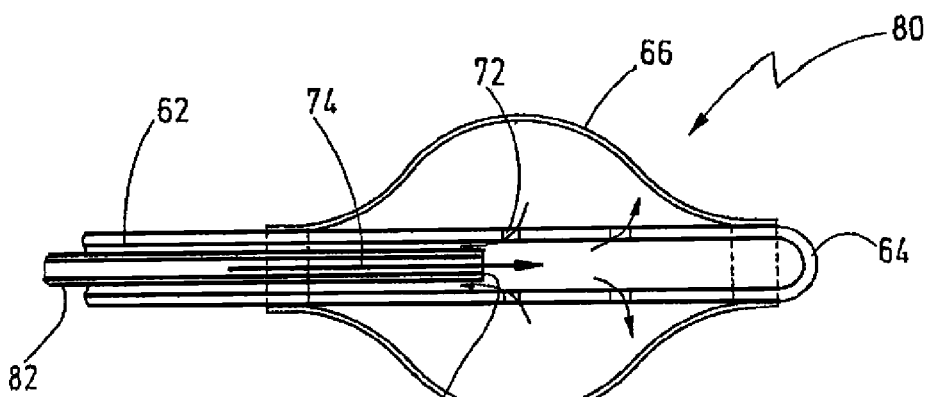
FIG. 5 shows a similar view of a fifth embodiment of a balloon catheter.

FIG. 5 shows a similar fifth embodiment of a balloon catheter 80.

The balloon catheter 80 has a shaft 62 with a closed end 64.

An inner tube 82 which is inserted into the shaft 62 ends at a distance to the closed end 64 of shaft 62 approximately at a height which is half the length of the balloon 66. This embodiment works similar to the embodiment shown in FIG. 4, but it is easier to manufacture, since the inner tube 82 has to be inserted only up to a certain extent into the shaft 62.

Figure 6:
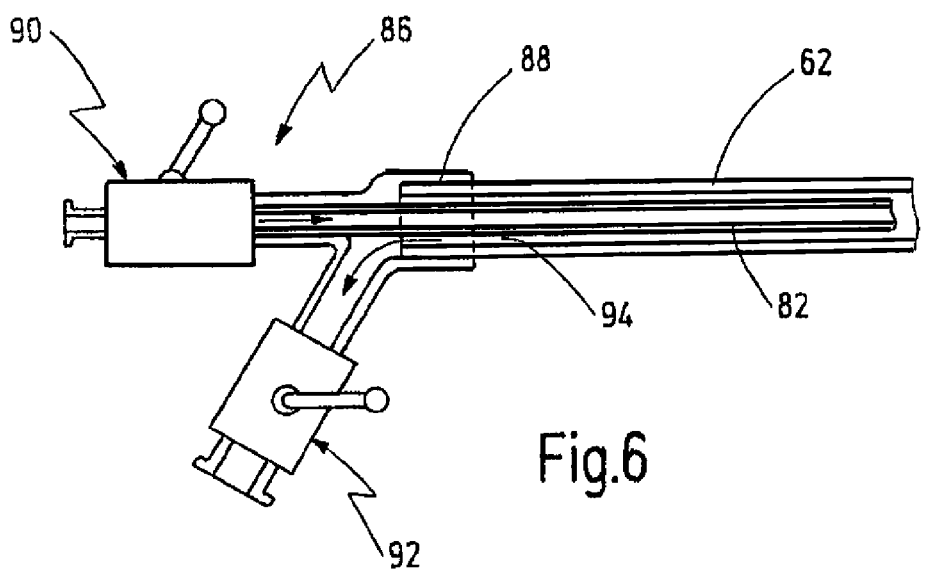
FIG. 6 shows a fitting attached to the proximal end of the balloon catheters shown in FIGS. 3 through 5.

FIG. 6 shows a fitting 86 which can be fitted to the proximal ends of the balloon catheter 50 shown in FIG. 3, the balloon catheter 60 shown in FIG. 4 or the balloon catheter 80 shown in FIG. 5.

As shown in FIG. 6, the fitting 86 is mounted to the outside of the proximal end of the shaft 62. If the fitting 86 is made from plastic, it is glued. The roughening 88, as described above, supports a fixing of these two different materials, metal and plastic, at the roughening 88. The inner tube 54 or 68 or 82 is connected to a LUER-lock 90, the branched LUER-lock 92 is connected to the channel 59 or 76 or 94.

Hoses can be connected to the thermal ends of the LUER-locks 90 and 92. When inserting a liquid inflating medium via the LUER-lock 90, the LUER-lock 92 is open, allowing the air to escape. If one recognizes liquid escaping from LUER-lock 92, one can assume that no more air is in the system, and the LUER-lock 92 can be closed. Inserting more and more liquid through LUER-lock 90 increases the pressure and the size of the balloon 66.

FIG. 7 shows a sixth embodiment of a balloon catheter 100.

The balloon catheter 100 has a flexible shaft 102 with a closed distal end 104 which is similar to the shaft 12 shown in FIG. 1. A balloon 106 is mounted as described above. An inner tube 108 is inserted into the flexible shaft 102. But, the distal end 116 of the inner tube 118 lies at the proximal end of the balloon 106. Holes 118 in the shaft 102 allow an inflating medium passing into the balloon 106. With the embodiment shown in FIG. 7, the inflating medium is fed via the LUER-lock 114 to the supply channel 112 between the outside of the inner tube 108 and the inner side of the shaft 102. Air in the system can escape via inner tube 118 to the LUER-lock 110.

FIG. 8 shows a seventh embodiment of a balloon catheter 120.

The balloon catheter 120 has a flexible shaft 122 having a rounded closed distal end 124.

A balloon 126 having one open end 128 only is mounted over the closed distal end area of the shaft 122. A neck is glued in a roughened area of the flexible shaft 122. Holes 129 allow an inflating medium to penetrate into the interior of the balloon 126. The balloon 126, when not inflated, lies around the rounded end surface of the shaft 122. In FIG. 8, the balloon 126 is shown in its inflated condition. The flexible shaft 122 is made of a steel alloy and has an outer diameter of 0.35 mm and an inner diameter of 0.22 mm.

FIG. 9 shows an eighth embodiment of a balloon catheter 130.

The balloon catheter 130 has a flexible shaft 132 which is a metal tube open on both sides. A balloon 136 is mounted to the open distal end 134 similar as described in connection with FIG. 8.

An illumination rod 138 having a diffusion tip 140 is inserted into the shaft 132. The diffusion tip 140 extends beyond the open distal end 134 of the shaft 132 and lies within the inflated balloon 136. A supply channel 142 is present between the outer side of the illumination rod 138 and the inner side of the shaft 132.

Light 144 emitted by the illumination rod 138 can be used either for Photo Dynamic Diagnosis (PDD) or Photo Dynamic Therapy (PDT). If the inflated balloon 136 is inflated with a liquid, this liquid supports diffusing of the light 144. A sensor 154 is mounted at the open end 134 of the shaft 132. The sensor 154 can detect the temperature of the liquid within the balloon 136 to avoid an overheating due to the emitted light. If the sensor 154 can detect flow, it works as a leakage control for supervising the balloon 136 leakage.

FIG. 10 shows that a so-called Tuohy Borst Y-connector 156 is attached to the proximal end of the shaft 132. This can again be done in the roughened area by gluing the connector 146 which is usually made of plastic.

The connector 146 has a side port 148 for inserting an inflating medium 150 into the supply channel 142. The connector 140 is provided with a screw fit 152 allowing to fix the illumination rod 138 in a certain axial position, for example as shown in FIG. 10.

Figure 11:
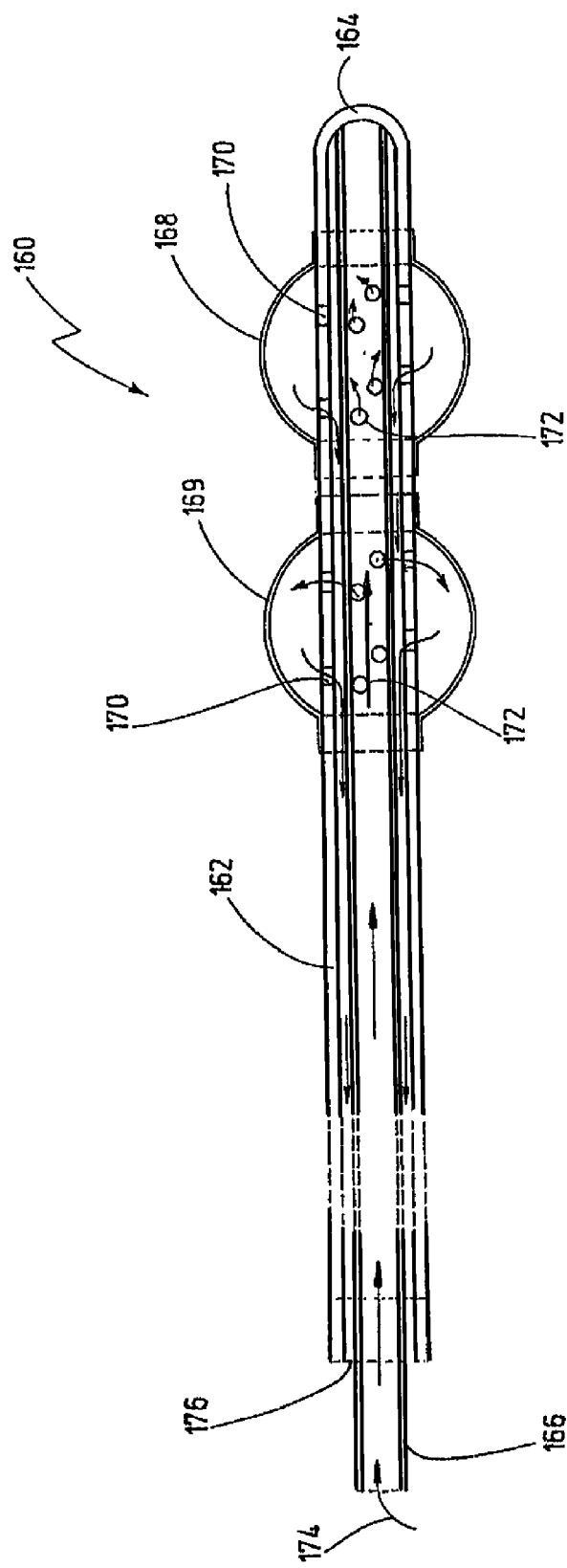
FIG. 11 shows a ninth embodiment of a balloon catheter with two balloons.

FIG. 11 shows a ninth embodiment of a balloon catheter 160. The balloon catheter 160 is similar to the construction shown in FIG. 4 and has a flexible shaft 162 with a closed rounded distal end 164. An inner tube 166 is inserted into the shaft 162 and extends up to the distal end 164.

Two balloons 168 and 169 are mounted at the outer side of the flexible shaft 162 as described before. Holes 170 in the flexible shaft 162 and holes 172 in the inner tube 166 communicate with the balloons 168, 169.

If an inflating medium 174, for example a liquid, is inserted into the inner tube 161, it penetrates the holes 172 and 170 and inflates the two balloons 168 and 169.

Air in the system can escape via escape channel 176. When deflating the balloons 168, 169, it is possible to insert air into the escape channel 176 for discharging the liquid via the inner tube 166.

Figure 12:
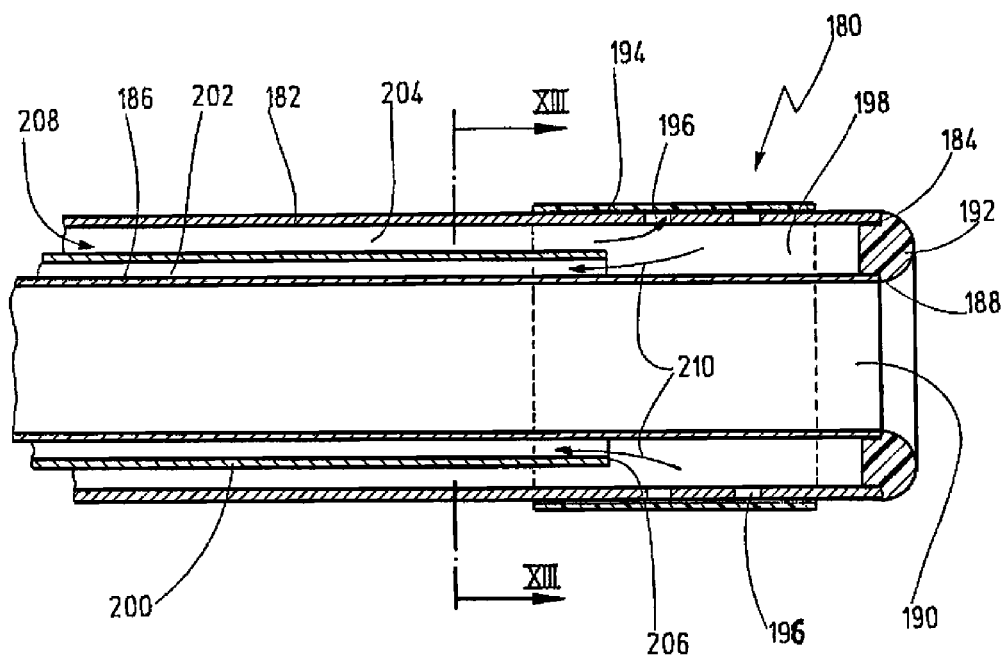
FIG. 12 shows a longitudinal section of a proximal end of a tenth embodiment of a balloon catheter.
Figure 13:
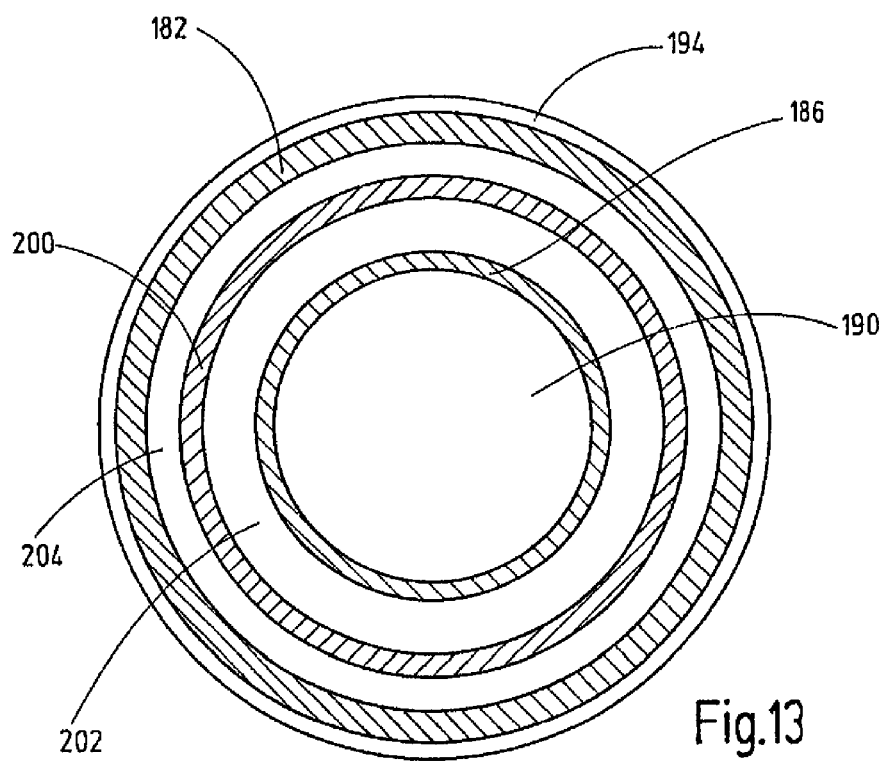
FIG. 13 shows a section along line XIII-XIII in FIG. 12.

FIGS. 12 and 13 show a tenth embodiment of a balloon catheter 180.

Balloon catheter 180 has an outer flexible shaft 182 which is a tube having an open distal end 184. An inner tube 186 is inserted into the flexible shaft 182.

A distal end 188 of inner tube 186 ends at the same height as the distal end 184 of the flexible shaft 182.

A ring closure 192 closes a distal end of a supply channel 198 existing between the outer side of the inner tube 186 and the inner side of the flexible shaft 182. The ring closure 192 is rounded and made of plastic, to provide an atraumatic distal end of the balloon catheter 180. A balloon 194 is mounted on the outer side of the flexible shaft 182. The balloon 194 has again the design of a hose section. Holes 196 in the flexible shaft 182 communicate with the balloon 194.

A further tube 200 is inserted into the supply channel 198.

The distal end 206 of the further tube 200 lies at a proximal end of the balloon 194.

The further tube 200 divides the supply channel 198 into a first inner subchannel 200, 202 and a second outer subchannel 204.

The flexible shaft 182 is made of stainless steel or nitinol and has an outer diameter of 0.5 mm and an inner diameter of 0.4 mm. The inner tube 186 has an outer diameter of 0.28 mm and an inner diameter of 0.20 mm and can be made of metal or of polyimide.

The further tube 200 is made of polyimide and has an outer diameter of 0.38 mm and an inner diameter of 0.33 mm.

As shown in FIG. 12, an inflating medium 208, for example a liquid, can be inserted into the outer second subchannel 204 which penetrates holes 196 and inflates the balloon 194. Air 210 in the lumen of the balloon catheter 110 can escape via inner first subchannel 202. The central working channel 190 is always free for inserting instruments or the like for performing manipulations.

The features "pressure sensor", "analyzer", "temperature sensor", and "leakage flow" were described in connection with particular embodiments. But, it can be realized in all of the described embodiments and in all combinations thereof. The temperature sensor can be mounted outside the balloon or inside the balloon for measuring the actual temperature. If mounted inside the balloon, the sensor is protected mechanically by the balloon body. In both mountings an exact temperature measurement is possible.

The invention claimed is:

1. Balloon catheter comprising an elongated flexible shaft and at least one inflatable balloon mounted on a distal end area of said flexible shaft, wherein a wall of said shaft providing mechanical properties for flexibility and pushability is entirely made of a metal, wherein said wall has a sheet-like shape, wherein said wall has an outer diameter up to 0.5 mm and a wall thickness in a range from 0.02 mm to 0.1 mm, and wherein an inner tube is housed in said shaft, said inner tube is closed at its distal end and said inner tube and said shaft are provided with openings in an area where said at least one balloon is mounted thereon.

2. Balloon catheter of claim 1, wherein said outer diameter of said wall of said shaft is selected from the group of outer diameters of less than 0.4 mm, less than 0.3 mm or less than 0.2 mm.

3. Balloon catheter of claim 1, wherein said wall thickness of said shaft is selected from the group of wall thicknesses of at least 0.025 mm, at least 0.03 mm and at least 0.04 mm.

4. Balloon catheter of claim 1, wherein said metal is selected from the group of stainless steel, a metal alloy, a nickel-titanium alloy.

5. Balloon catheter of claim 1, wherein a distal end of said shaft is closed, and wherein said wall of said shaft has said openings of said shaft in the distal end area thereof, wherein said balloon is mounted.

6. Balloon catheter of claim 1, wherein a flexible tip projects distally from a distal end of said shaft.

7. Balloon catheter of claim 6, wherein said tip is a flexible guide wire.

8. Balloon catheter of claim 7, wherein said tip has a diameter which is smaller than said outer diameter of said shaft.

9. Balloon catheter of claim 1, wherein an outer diameter of said inner tube is smaller than an inner diameter of said shaft, defining a supply channel for supplying an inflating medium into said balloon, said supply channel opens into said at least one balloon.

10. Balloon catheter of claim 1, wherein said at least one balloon has a shape of a hose section having two opposite ends, said hose section is mounted via its two opposite ends on an outer surface of said shaft.

11. Balloon catheter of claim 1, wherein an outer surface of said shaft is roughened in at least an area where said at least one balloon is mounted thereon.

12. Balloon catheter of claim 1, wherein said shaft is roughened on its proximal end.

13. Balloon catheter of claim 1, wherein a balloon having one open end is mounted with said open end at a distal end of said shaft.

14. Balloon catheter of claim 1, wherein said inner tube is mounted in said shaft defining a supply channel therebetween, wherein a further tube is mounted in said shaft supply channel, said further tube divides said supply channel into two subchannels, each of said subchannels is in communication with each of said at least one balloon.

15. Balloon catheter of claim 14, wherein each of said subchannels is connected at its proximal end to a fitting.

16. Balloon catheter of claim 1, wherein said shaft is, at its outer side, made of a material of a low slide resistance.

17. Balloon catheter of claim 1, wherein said shaft is, at its outer side provided with a drug.

18. Balloon catheter of claim 1, wherein at least one sensor is provided.

19. Balloon catheter of claim 18, wherein said at least one sensor is selected from the group existing of pressure sensors, temperature sensors, analyzers and leakage flow sensors.

20. Balloon catheter comprising an elongated flexible shaft and at least one inflatable balloon mounted on a distal end area of said flexible shaft, wherein a wall of said shaft providing mechanical properties for flexibility and pushability is entirely made of a metal, wherein said wall has a sheet-like shape, wherein said wall has an outer diameter up to 0.5 mm and a wall thickness in a range from 0.02 mm to 0.1 mm, wherein an inner tube is mounted in said shaft defining a supply channel therebetween, and wherein a further tube is mounted in said shaft supply channel, said further tube divides said supply channel into two subchannels, each of said subchannels is in communication with each of said at least one balloon.

21. Balloon catheter of claim 20, wherein each of said subchannels is connected at its proximal end to a fitting.

22. Balloon catheter of claim 20, wherein said outer diameter of said wall of said shaft is selected from the group of outer diameters of less than 0.4 mm, less than 0.3 mm or less than 0.2 mm.

23. Balloon catheter of claim 20, wherein said wall thickness of said shaft is selected from the group of wall thicknesses of at least 0.025 mm, at least 0.03 mm and at least 0.04 mm.

24. Balloon catheter of claim 20, wherein said metal is selected from the group of stainless steel, a metal alloy, a nickel-titanium alloy.

25. Balloon catheter of claim 20, wherein a distal end of said shaft is closed, and wherein said wall has holes in a distal end area thereof, wherein said balloon is mounted.

26. Balloon catheter of claim 20, wherein a flexible tip projects distally from a distal end of said shaft.

27. Balloon catheter of claim 26, wherein said tip is a flexible guide wire.

28. Balloon catheter of claim 27, wherein said tip has a diameter which is smaller than said outer diameter of said shaft.

29. Balloon catheter of claim 20, wherein said inner tube is housed in said shaft, said inner tube is open on its distal end and defines a central working channel passing through said shaft.

30. Balloon catheter of claim 29, wherein an outer diameter of said inner tube is smaller than an inner diameter of said shaft, thereby defining a supply channel for supplying an inflating medium to said balloon, said supply channel opens into said balloon.

31. Balloon catheter of claim 20, wherein said inner tube is housed in said shaft, said inner tube is closed at its distal end and said inner tube and said shaft are provided with openings in an area where said at least one balloon is mounted thereon, and wherein an outer diameter of said inner tube is smaller than an inner diameter of said shaft, defining a supply channel for supplying an inflating medium into said balloon, said supply channel opens into said at least one balloon.

32. Balloon catheter of claim 20, wherein said inner tube is housed in said shaft, said shaft is closed at its distal end, and said inner tube is open at its distal end, and wherein said inner tube ends at a distance at said closed end of said shaft.

33. Balloon catheter of claim 20, wherein said at least one balloon has a shape of a hose section having two opposite ends, said hose section is mounted via its two opposite ends on an outer surface of said shaft.

34. Balloon catheter of claim 20, wherein an outer surface of said shaft is roughened in at least an area where said at least one balloon is mounted thereon.

35. Balloon catheter of claim 20, wherein said shaft is roughened on its proximal end.

36. Balloon catheter of claim 20, wherein a balloon having one open end is mounted with said open end at a distal end of said shaft.

37. Balloon catheter of claim 20, wherein said shaft is, at its outer side, made of a material of a low slide resistance.

38. Balloon catheter of claim 20, wherein said shaft is, at its outer side provided with a drug.

39. Balloon catheter of claim 20, wherein at least one sensor is provided.

40. Balloon catheter of claim 39, wherein said at least one sensor is selected from the group existing of pressure sensors, temperature sensors, analyzers and leakage flow sensors.

* * * * *